United States Patent [19]

Down et al.

[11] 4,434,133
[45] Feb. 28, 1984

[54] SYSTEM FOR THE PRODUCTION OF KETENE AND METHYLENE FROM CARBONATE MINERALS

[75] Inventors: Michael G. Down, Plum Borough; D. Colin Phillips, Monroeville; Werner S. Emmerich, Churchill Borough, all of Pa.

[73] Assignee: Westinghouse Electric Corp., Pittsburgh, Pa.

[21] Appl. No.: 266,671

[22] Filed: May 26, 1981

[51] Int. Cl.³ .............................................. G21C 15/00
[52] U.S. Cl. ...................................... 376/323; 568/301
[58] Field of Search ................................. 376/323–325, 376/148; 568/301, 409; 585/535; 204/158 R, 204/158 E

[56] References Cited

U.S. PATENT DOCUMENTS

| | | | |
|---|---|---|---|
| 1,910,815 | 5/1933 | Schlecht | 568/409 |
| 1,926,642 | 9/1933 | Young et al. | 568/301 |
| 3,558,724 | 1/1971 | Salotti | 260/676 |
| 4,009,219 | 2/1977 | Tamers | 423/439 |
| 4,132,727 | 1/1979 | Gomberg | 376/324 |
| 4,140,600 | 2/1979 | Gomberg | 376/148 |
| 4,140,602 | 2/1979 | Lewis et al. | 376/148 |
| 4,158,637 | 6/1979 | Jones | 376/324 |
| 4,314,448 | 2/1982 | Alefeld | 376/323 |

FOREIGN PATENT DOCUMENTS

| | | | |
|---|---|---|---|
| 53793 | 12/1981 | European Pat. Off. | 568/301 |
| 388402 | 2/1933 | United Kingdom | 568/409 |
| 701550 | 12/1953 | United Kingdom | 568/409 |

OTHER PUBLICATIONS

"Acetylene Homologs and Derivatives," Piganiol, N.Y. (1950), pp. 155–169.
"Organic Chemistry," Morrison and Boyd, Boston (1966), pp. 132–135.

*Primary Examiner*—Sal Cangialosi
*Attorney, Agent, or Firm*—D. P. Cillo

[57] ABSTRACT

Organic hydrocarbon materials are produced from plentiful inorganic limestone type materials by: (1) reacting the limestone type materials with molten lithium metal to produce $Li_2C_2$, (2) hydrolyzing the $Li_2C_2$ to produce $C_2H_2$, (3) catalytically reacting the $C_2H_2$ with steam to produce $CH_3COCH_3$, (4) pyrolyzing the $CH_3COCH_3$ to provide ketene and methane, and separating the ketene. The ketene may then be decomposed to provide methylene, which can be reacted with an alkane, such as methane in an insertion chain reaction, to provide organic hydrocarbon materials. An in-place nuclear reactor can provide energy for the endothermic reactions of the system.

14 Claims, 2 Drawing Figures

SYSTEM FOR THE PRODUCTION OF KETENE AND METHYLENE FROM CARBONATE MINERALS

BACKGROUND OF THE INVENTION

Coal can be efficiently converted into hydrocarbons of a more useful gaseous or liquid form by coal gasification or liquefaction techniques, utilizing energy from a high-temperature, gas-cooled nuclear reactor for the endothermic and/or electrolytic processing required, as taught by Jones, in U.S. Pat. No. 4,158,673. While the United States, the Soviet Union, and China still contain major deposits of coal, this mineral is considered precious in most other parts of the world, where deposits are either lacking or have been largely used up.

Thus, while the earth's supply of precious fossil fuels is being steadily depleted to provide electricity and petrochemicals, a virtually unlimited worldwide supply of other carbon bearing minerals remains untapped as an energy source. Salotti, in U.S. Pat. No. 3,558,724, taught that inorganic crystalline carbonates could provide gaseous products containing up to 4% methane, if the carbonates were first heated in an oxygen-free atmosphere at from about 400° C. to 700° C., and then contacted with excess hydrogen gas at from about 200 psi. to 10,000 psi. This process, however, uses large quantities of valuable hydrogen gas, which is becoming increasingly important itself as an energy source. In addition, this process provides a poor yield of methane, leaves carbon residue and maintains explosive reaction conditions.

Tamers, in U.S. Pat. No. 4,009,219, taught the production of benzene from inorganic carbonates such as limestone. Tamers reacted limestone ($CaCO_3$) with lithium metal in a vacuum at 500° C., raised the temperature of reaction to 1,000° C. for 30 minutes to reverse secondary reactions that produce carbon and metal oxide, and then hydrolyzed the resulting product lithium carbide ($Li_2C_2$) with water. This produced acetylene, with calcium oxide and lithium hydroxide by-products. The lithium hydroxide was converted to lithium metal by fused salt electrolysis, and recycled back to the limestone reaction. The acetylene was then purified and dried. Benzene was produced from this treated acetylene, using dried potassium chromate activated silica-alumina catalyst at 120° C. to 200° C. Benzene, however, is now known to be toxic and a carcinogenic agent.

What is needed is a method to produce high carbon chain hydrocarbons without using valuable fuels such as coal or hydrogen or producing toxic substances such as benzene.

SUMMARY OF THE INVENTION

It has been discovered that the above-described need can be met by a process comprising the steps of: (1) reacting inorganic, crystalline or non-crystalline, carbon containing mineral material, such as $CaCO_3$, with a stoichiometric excess of molten lithium metal, in a lithium reactor means, in an inert atmosphere, at a temperature of between about 300° C. and about 1,200° C., to provide lithium salt compounds such as $Li_2C_2$ and $Li_2O$, and formation of CaO; (2) hydrolyzing the $Li_2C_2$ to provide $C_2H_2$ (acetylene gas). A lithium hydroxide slurry formed from the $Li_2O$ can be recovered from the hydrolysis step and converted to lithium metal by a variety of means, such as fused salt electrolysis, for recycle to the lithium reactor means; (3) reacting the $C_2H_2$ with steam at between about 250° C. and about 475° C. in the presence of catalysts such as ZnO, to provide $CH_3COCH_3$ (acetone). The $C_2H_2$ does not have to be purified for this reaction to occur; (4) pyrolyzing the $CH_3COCH_3$ at between about 600° C. and about 800° C., to provide ketene gas, which is then cooled to −60° C. by a suitable cooling means, to provide a ketene product ($CH_2=C=O$) in liquid form, and separable methane gas. The ketene can then be stored as a liquid at 25° C. under a pressure of about 40 psi, if desired.

In reduction step (1) and hydrolysis step (2), a total of approximately 976 kJ. of energy is gained for each mole of $CaCO_3$ used. Some of this energy can be used to keep the lithium reactor at temperature. The CaO still present in step (2) can be separated from the lithium hydroxide slurry for use in other industries, such as an alkali for water treatment, etc. By-product hydrogen from step (3) and methane from step (4) can be separated and used as fuels. The electrolysis step to provide lithium metal, and the pyrolysis step to provide ketene require a large expenditure of energy, which could be supplied by a pressurized water nuclear reactor, or a high-temperature, gas-cooled nuclear reactor, without major modifications in design or structure of the reactor. Energy from the nuclear reactor could also be used to help keep the lithium reactor at temperature, and to provide steam and heat to produce acetone from acetylene. Thus, uranium would be the chief fuel consumed in the process of converting the inorganic carbon into an organic carbon, which can be used to produce liquid hydrocarbon fuels such as diesel oil or gasoline.

The ketene can be photochemically decomposed or thermally decomposed to produce extremely reactive, organic methylene. A particular type of insertion chain reaction sequence could then be started between methylene and alkanes, such as methane, which could be easily supplied as a by-product from the pyrolysis reaction. This could ultimately result in a mixture of ethane, propane, butane, pentane, hexane, heptane, and possibly higher carbon chain hydrocarbons such as octane. The pyrolysis of acetone, the decomposition of ketene and the methylene insertion chain reaction to form ethane and higher hydrocarbons, can be accomplished as separate steps, or they can be combined in various fashions. Thus, by the method of this invention, limestone type minerals can be reacted to form gasoline-type molecules via a ketene reaction sequence, utilizing energy from an already existing nuclear power source.

BRIEF DESCRIPTION OF THE DRAWING

For a better understanding of the invention, reference may be made to the preferred embodiments, exemplary of the invention, shown in the accompanying drawings, in which.

DESCRIPTION OF THE PREFERRED EMBODIMENTS

Figure 1:
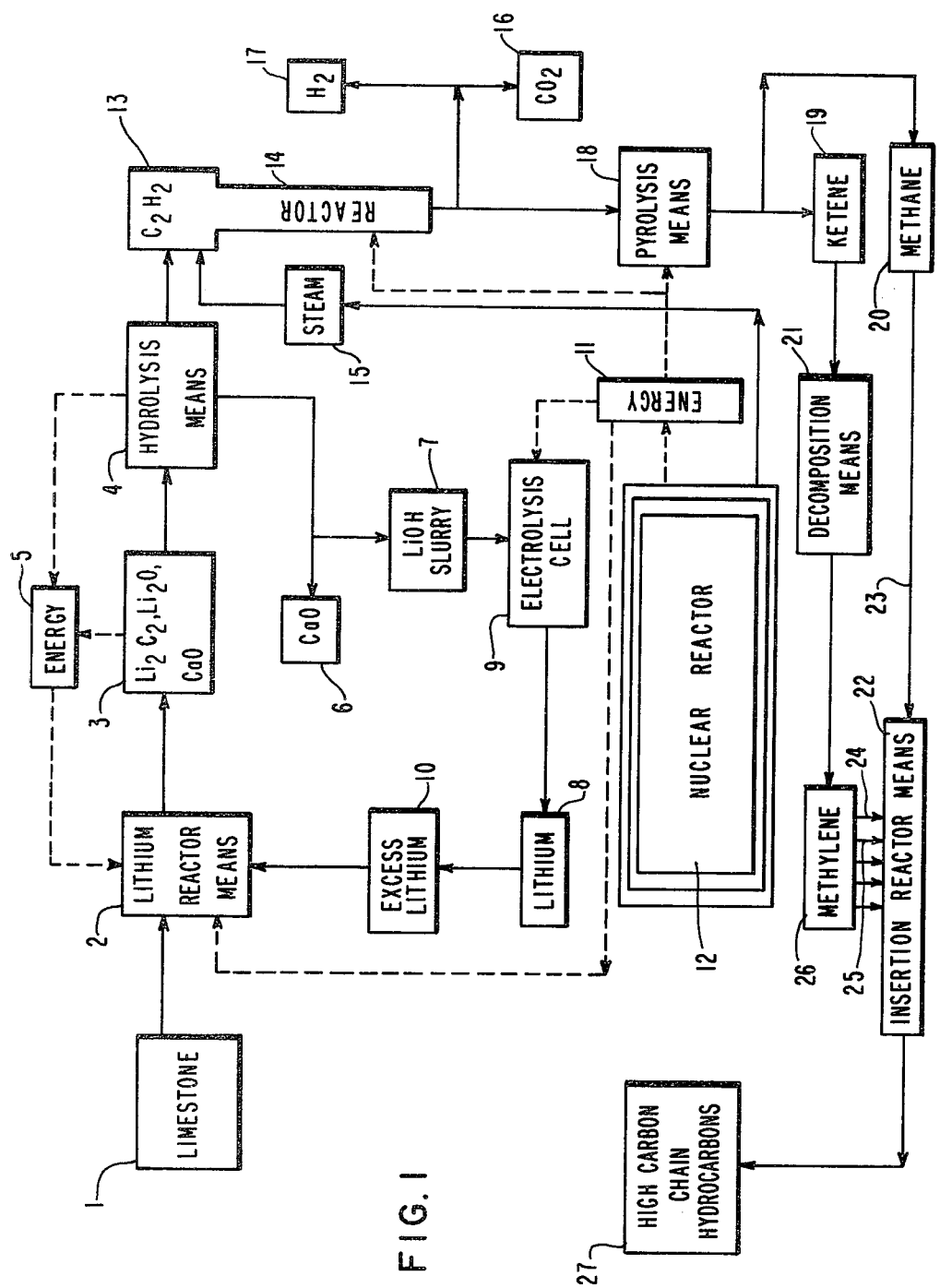
FIG. 1 is a flow chart of one embodiment of the system of this invention.

The starting material 1, for the system of this invention, shown in FIG. 1 of the Drawings, is an inorganic, crystalline or non-crystalline, carbon containing mineral material. These are usually carbonate containing materials, preferably a limestone type ($CaCO_3$). Useful carbonates are selected from: calcite ($CaCO_3$), dolomite ($CaMg(CO_3)_2$), siderite ($FeCO_3$), magnesite ($MgCO_3$), rhodochrosite ($MnCO_3$), smithsonite ($ZnCO_3$), arajonite ($CaCO_3$), witherite ($BaCO_3$), strontianite ($SrCO_3$), cerussite ($PbCO_3$), malachite ($CuCO_3(OH)_2$), azurite ($Cu_3(CO_3)_2(OH)_2$), their mixtures, and the like.

These carbonate materials, alone or in mixtures, are fed into a heated, sealed, leak-free, lithium reactor means 2, which is made from a non-reactive material such as stainless steel. Molten lithium is contained in the vessel, which also usually contains an inert atmosphere, such as argon or helium, over the molten metal. This reactor vessel may have a mechanical stirrer, or a rotating magnet disposed under the vessel, effective to cause stirring of the lithium metal in the vessel. Air and moisture are excluded from the vessel which operates at a temperature of between about 300° C. to about 1,200° C. The exothermic interaction in the lithium reactor, which helps maintain sufficient reactor temperature, comprises the following chemical reaction when $CaCO_3$ is the starting material:

$$CaCO_3 + excess\ Li \rightarrow CaO + Li_2C_2 + Li_2O \qquad (1)$$

In this reaction, over 5 moles of Li per mole of limestone is used. While this and subsequent reactions start with $CaCO_3$, other of the above-described feed materials would follow a corresponding process.

Liquid lithium (m.p.=180.5° C.) provides a highly reactive, relatively low temperature reducing medium which provides the following lithium salts:

|  | HEAT OF REACTION |
|---|---|
| $Li + C \rightarrow Li_2C_2$ (lithium carbide) | $-59.4$ kJ. mol$^{-1}$ |
| $Li + O \rightarrow Li_2O$ (lithium oxide) | $-587.9$ kJ. mol$^{-1}$. |

These salts are highly stable. In particular, the high negative value for the free energy of formation of lithium oxide provides the driving force which results in the decomposition of almost all oxygen containing inorganic compounds when reacted with liquid lithium. In reaction (1), the very high stability of CaO, which is even more stable than lithium oxide, reinforces this effect and results in a highly exothermic reaction, having a heat of reaction of about $-1,313$ kJ. While the lithium provides a means of decomposing the limestone, it also traps the liberated carbon by formation of the stable species $Li_2C_2$ (lithium carbide or lithium acetylide).

The stability of these salts, and use of excess stoichiometric amounts of lithium, precludes the formation of compounds containing hetero-atomic anions, such as $LiCO_3$, which do not readily hydrolyze to provide useful fuel gases. By "stoichiometric excess of lithium," is meant an amount of from 2 mole% to 200 mole%, preferably 75 mole% to 125 mole%, of Li in excess of that required to completely react with all the total C and O present. The reaction, accompanied by constant stirring, is completed in about ¾ hour to 1½ hours, preferably at a temperature of between about 700° C. and 900° C., resulting in a top liquid phase consisting of molten lithium, and a bottom solid reaction product phase usually consisting of the $Li_2C_2$, and $Li_2O$ salts and the CaO. The excess lithium is then cooled to about 300° C. before being drawn off, and then the reaction product solids are allowed to cool. The cooled reaction product solids 3 are then either transferred to another vessel 4 for hydrolysis, or left in place so that hydrolysis is accomplished in the same vessel.

Lithium carbide is still an inorganic, strongly ionic material, being composed of $C_2^{2-}$ anions and $Li^+$ cations. The conversion of this material into a purely organic, covalent material can be achieved by the hydrolysis of the products from reaction (1), at about 25° C., to provide the following materials:

|  | HEAT OF REACTION |
|---|---|
| (2) $Li_2C_2 + 2H_2O \rightarrow C_2H_2 + 2LiOH$ | $-113$ kJ. mol$^{-1}$ |
| $Li_2O + H_2O \rightarrow 2LiOH$ | $-132$ kJ. mol$^{-1}$ |

These exothermic reactions, in conjunction with the heat evolved by the reduction step of reaction (1), lead to a total energy gain of 976 kJ. for every mole of $CaCO_3$ consumed, or every ½ mole of $C_2H_2$ (acetylene) produced. Some of this energy 5 will be used to keep the lithium reactor at temperature, and the remainder could be used to help power other parts of the overall reaction system. The hydrolysis reaction temperatures must be controlled by removal of heat, otherwise the acetylene could polymerize or decompose.

The hydrolysis steps result in a suspension of an oxide, such as calcium oxide (quicklime) in an aqueous solution of lithium hydroxide. The quicklime 6 is separated for use in other industries, such as an alkali for water treatment, etc. The lithium hydroxide slurry 7 is reprocessed to produce lithium metal 8, for example, by electrolysis of fused chloride in electrolysis cell 9 at about 410° C. to 450° C., after a suitable conversion step, as shown by the following chemical reactions:

$$2LiOH + CO_2 \rightarrow Li_2CO_3 + H_2O$$

$$Li_2CO_3 + Cl_2 \rightarrow 2LiCl + CO_2 + \tfrac{1}{2}O_2$$

$$2LiCl(electrolysis) \rightarrow 2Li + Cl_2$$

The overall reaction is:

$$2LiOH \rightarrow 2Li + H_2O + \tfrac{1}{2}O_2 \qquad (2)$$

Excess of this lithium 10, would be recycled into the lithium reactor means. Each pound of lithium metal recycled in this way would require about 1,750 amp-hours and a sufficient voltage to dissociate the chloride, approximately 2.5 volts. This electrolysis step represents consumption of major amounts of energy 11, which may be supplied by an in-place nuclear reactor 12, as described hereinbelow. Any other method known to the art could of course be used to produce lithium metal from the hydroxide, to close the limestone/lithium cycle.

After the acetylene producing hydrolysis, the acetylene gas 13, which need not be either dried or purified, is passed through a heated, gas tight, steel reactor tube 14, having steam inlet means 15 and gas outlet means. Here the acetylene gas will undergo ketonization hydrolysis in the presence of a catalyst, such as zinc oxide, zinc vanadate, or their mixtures, at between about 250° C. and 450° C., to form acetone ($CH_3COCH_3$) according to the following chemical reaction:

$$2C_2H_2 + 3H_2O \rightarrow CH_3COCH_3 + CO_2 + 2H_2 \qquad (3)$$

ketene in a separate low temperature step, as described above. At the first methylene inlet 24, the following chemical reaction would occur to produce ethane:

$$CH_3H + CH_2 \rightarrow CH_3CH_3$$

The ethane formed would then be contacted with methylene from the adjacent spaced apart downstream inlet 25, and the following chemical reaction would occur to produce propane:

$$CH_3CH_2H + CH_2 \rightarrow CH_3CH_2CH_3$$

In this manner, butane, pentane, hexane, heptane and possibly octane would be formed. Thus, a methylene-alkane insertion chain reaction would be produced, to provide a high carbon chain hydrocarbon gas and/or liquid mixture 27.

Figure 2:
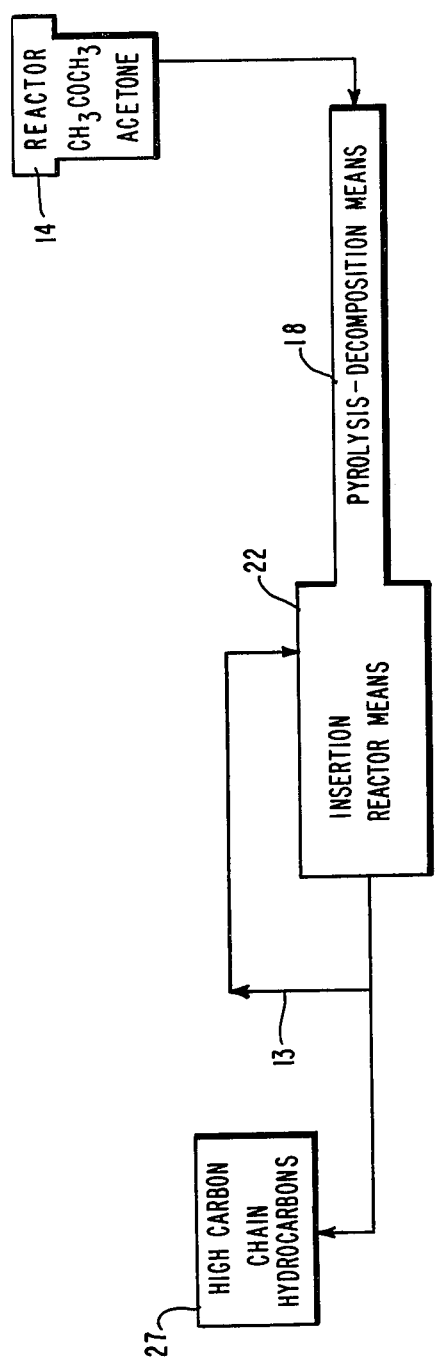
FIG. 2 is a flow chart of another embodiment of the method of this invention where pyrolysis and decomposition means are combined.

Gasoline is a mixture of hydrocarbons comprising heptanes, octanes, etc.; thus, by this process, inexpensive and plentiful carbonate type materials can be reacted to form gasoline-type molecules via a ketene reaction sequence and utilizing existing nuclear energy. It is also possible to combine the pyrolysis means and the decomposition means, and pyrolyze acetone and decompose the ketene product in a single stainless steel tube, maintained at about 600° C. to about 800° C., feeding directly into insertion reactor means. In this embodiment, the methane and carbon monoxide byproducts formed would directly feed into the insertion reactor means with the methylene, as shown in FIG. 2 of the Drawings. While this would save ketene condensation, the methane would not be reacted with methylene in sequence, as shown in FIG. 1, and so longer chain hydrocarbons such as octane might not be formed. This could be alleviated by recycling a major portion of the formed hydrocarbons via line 13 back into the insertion reactor means where they could further react with methylene.

Other reactions of methylene, that can be used to produce hydrocarbons, include reactions with ketene as follows, to form ethylene, ethane, acetylene and/or propane:

$$CH_2CO + CH_2 \rightarrow CH_2=CH_2 + CO$$

$$CH_2CO + CH_2 \rightarrow CH_3 + CHCO$$

$$2CH_3 \rightarrow C_2H_6$$

$$2CHCO \rightarrow CH\equiv CH + 2CO$$

$$C_2H_4 + CH_2 \rightarrow C_3H_6$$

Methylene readily adds cross carbon-carbon double bonds. The simplest reaction involves the addition of methylene to ethylene to form cyclopropane and propylene:

$$CH_2=CH_2 + CH_2 \longrightarrow$$

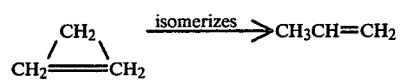

Alternatively, acetylene can be reacted with methylene to form cyclopropene and allene, according to the chemical reaction:

$$CH\equiv CH_3 + CH_2 \longrightarrow$$

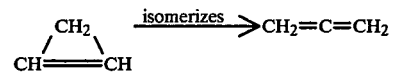

It is to be understood, that while $CaCO_3$ is the preferred carbon containing mineral feed, and the reactions have been described particularly relating thereto, the other carbonate containing materials set forth hereinabove would provide equally outstanding end results.

We claim:

1. A process of converting inorganic carbonate mineral material to organic hydrocarbon material, comprising the steps of:
   (1) reacting inorganic carbonate mineral material with a stoichiometric excess of molten lithium metal, at a temperature over about 300° C. in the absence of air and moisture, to produce a product mixture comprising lithium salts $Li_2C_2$ and $Li_2O$, and then
   (2) hydrolyzing the lithium salts produced in step (1), to produce $C_2H_2$, and then
   (3) catalytically reacting the $C_2H_2$ produced in step (2), with steam, in the presence of zinc containing catalyst, in a manner effective to produce $CH_3COCH_3$, and then
   (4) pyrolyzing the $CH_3COCH_3$ produced in step (3), to provide ketene and methane, and then
   (5) separating ketene from methane.

2. The method of claim 1, where during the hydrolysis step (2), LiOH is also produced, and said LiOH is reacted to form lithium chloride, which is then electrolyzed to provide Li metal which is recycled back to step (1).

3. The method of claim 2, where the heat energy required for the pyrolyzing step to form ketene, and the electrolyzing step to form Li metal is supplied, at least in part, from a nuclear reactor.

4. The method of claim 2, where the catalyst used in step (3) is selected from the group consisting of zinc oxide, zinc vanadate, and mixtures thereof, where benzene is not produced in step (3), and the reaction in step (3) proceeds at between about 250° C. and about 475° C.

5. The method of claim 2, where after step (5), the ketene is decomposed to provide methylene.

6. A process of converting inorganic carbonate mineral material to organic high carbon chain hydrocarbon material, utilizing nuclear reactor energy, comprising the steps of:
   (1) reacting inorganic carbonate mineral material with a stoichiometric excess of molten lithium metal, at a temperature over about 300° C. in the absence of air and moisture, to produce a product mixture comprising lithium salts $Li_2C_2$ and $Li_2O$, and then
   (2) hydrolyzing the lithium salts produced in step (1), to produce $C_2H_2$, and then
   (3) catalytically reacting the $C_2H_2$ produced in step (2), with steam, in the presence of zinc containing catalyst, at between about 250° C. and about 475° C., in a manner effective to provide gases which upon condensation yield $CH_3COCH_3$, without producing benzene, and then The velocity of the gases through the tube should be about 450 to 1,000 liters/hour for tube diameters of about 125 mm. An excess of steam may be used, with yields of 80% to 95% at 450° C. The temperature can be maintained, for example, by use of a molten salt bath. This reaction is further described by P. Piganiol, Acetylene Homologs And Derivatives, New York, 1950, pp. 155 to 166.

The gas mixture is cooled to condense acetone liquid, usually at 25° C., and the remaining gases can be further separated, 16 and 17, to yield $CO_2$, and $H_2$, which can be used as a fuel. In this ketonization step, the zinc catalyst is essential to the production of acetone, since use of other catalysts will produce a variety of other end products, for example, alumina catalyst will produce cyclic furan

materials, and the deletion of catalyst yields cyclic paraldehyde $C_6H_{12}O_3$. The usual source of acetone is from petroleum. Isopropanol can be produced from petroleum hydrocarbon, and can in turn easly be converted to acetone. A combination acetylene ketonation reactor tube-condensation means is shown as 14 in FIG. 1 of the Drawings.

The cooled, liquid acetone is then pyrolyzed at between about 600° C. to about 800° C. in a stainless steel or other suitable furnace, shown as 18 in FIG. 1 of the Drawings. Here, the acetone is decomposed by heat alone without oxidation (pyrolysis), to produce ketene 19 and methane gas 20 according to the following overall chemical reaction:

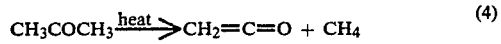

(4)

The gas mixture is then cooled to condense ketene liquid, usually at about −60° C. The by-product methane gas, which is separated from ketene, can be used as a fuel, or saved for further processing in the method of this invention. The cooling step here and in the formation of acetone can utilize, for example, a −70° C. bath of acetone and liquid nitrogen surrounding the condensation apparatus. Cooling water associated with a nuclear reactor could also be used. The ketene can be allowed to vaporize for further reactions after separation from methane.

The heat energy 11 required for reactions (1), (2'), (3) and (4), i.e., the molten lithium reactor, the electrolysis of lithium hydroxide, the formation of acetone, and the pyrolysis to form ketene, can be supplied by an in-place nuclear reactor 12. These endothermic demands can be met by relatively low-cost nuclear energy, derived, for example, from a very high-temperature, gas-cooled, nuclear reactor, or a liquid-cooled nuclear reactor, both well known in the art, and described in detail by Tobin, in U.S. Pat. No. 4,113,563, and Obenmeyer et al., in U.S. Pat. No. 4,173,513, respectively.

In the more common liquid-cooled nuclear reactor, a liquid reactor coolant, such as water, is pumped into the reactor pressure vessel enclosing the nuclear core. The pressurized water circulates around the core where heat energy is absorbed raising its temperature to about 400° C. The hot pressurized water is then passed out of the reactor vessel to a heat exchanger, typically referred to as a steam generator, in which the heat is transferred to a utilization circuit, such as a steam cycle driving turbine-generator apparatus, which produces electricity. The cooled water is then recirculated. The steam can be used in the acetylene reaction. The electricity can be used to maintain the lithium reaction and the electrolysis, acetone formation and pyrolysis reactions. The gas-cooled nuclear reactor would provide more easily obtainable energy since gas exit temperatures are well over 700° C.

Ketene is a useful material that can be made to undergo a variety of reactions to produce high carbon chain hydrocarbons. Ketene can be used to form methylene. The methylene can be reacted with methane by an insertion chain reaction technique, to provide hydrocarbons such as heptane and octane; the methylene can be reacted with ketene to provide ethylene, ethane, acetylene and/or propane; the methylene can be reacted with acetylene to provide cyclopropene and allene; and the methylene can be reacted with ethylene to provide cyclopropane and propylene. The most valuable of these reactions is the insertion chain reaction.

Once ketene has been produced, $CH_2$ (methylene or carbene) can be easily formed by photochemical decomposition in the 2,400 to 3,800 Angstrom unit region, using, for example, an ultraviolet light source, or by solar energy, or by thermal energy, which again can use the nuclear power plant as a source. This decomposition proceeds according to the chemical reaction:

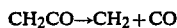

The methylene produced 26 may exist in two different spin states: one is where unshared electrons are paired, i.e., "singlet" methylene:

and the other is where the unshared electrons are not pared, i.e., "triplet" methylene

The triplet methylene is in fact a free diradical. The singlet form is the less stable and is the form usually first generated. The exact chemical properties of the methylene are affected by the reaction conditions used to produce it. Further details of this reaction and the methylene product can be found in Morrison and Boyd, Organic Chemistry, Boston, 1966, Ch. 4.33.

The decomposition means 21 can take the form of a pyrex glass tube, with a solar radiation source or a bank of suitable ultraviolet lamps, or a steel tube heated to a temperature of preferably between about 40° C. and about 75° C.

The carbon monoxide by-product of decomposition can remain with the methylene, without harming subsequent reactions. In the insertion means 22, preferably a long steel tube, methylene would be fed through line 23 at a flow rate of about 450 to 1,000 liters/hour for insertion reactor tube diameters of about 125 mm. The tube length could vary between about 15 to 30 meters, with a plurality of downstream methylene inlets about every 2 meters of length. The insertion reactor means could operate at 25° C. if methylene is converted from liquid (4) pyrolyzing the $CH_3COCH_3$ produced in step (3), at between about 600° C. and about 800° C., to provide ketene and methane, and then (5) separating ketene from methane, and then (6) decomposing the ketene to provide methylene, and then (7) reacting the methylene with an alkane material, to provide a product which is reacted with additional methylene in a manner effective to cause methylene insertion chain reactions and provide hydrocarbon materials containing at least three carbon atoms; where at least a part of the heat energy required for the pyrolyzing step of step (4) is supplied from a nuclear reactor.

7. The method of claim 6, where the carbonate mineral material is selected from the group consisting of calcite, dolomite, siderite, magnesite, rhodochrosite, smithsonite, arajonite, witherite, strontianite, cerussite, malachite, azurite, and mixtures thereof.

8. The method of claim 6, where during the hydrolysis step (2), LiOH is also produced, and said LiOH is reacted to form lithium chloride which is then electrolyzed to provide Li metal which is recycled back to step (1).

9. The method of claim 6, where the catalyst used in step (3) is selected from the group consisting of zinc oxide, zinc vanadate, and mixtures thereof, and the carbonate mineral material is limestone.

10. The method of claim 6, where ketene is separated from methane in step (5) by condensing ketene at about −60° C., after which it is allowed to vaporize.

11. The method of claim 6, where the ketene after step (5) is in vapor form, and is decomposed in step (6) by heat and/or light energy.

12. The method of claim 6, where the alkane reacting with methylene in step (7) is methane supplied at least in part from step (4), and where the methane reacts with methylene to form ethane, the ethane reacts with methylene to form propane, and the propane reacts with methylene to form butane; said methane being fed into a long tube reactor having a plurality of spaced apart downstream methylene inlets.

13. The method of claim 6, where the nuclear reactor utilized is liquid-cooled nuclear reactor.

14. The method of claim 8, where the energy required for the electrolyzing step to form Li metal, is supplied in part from a nuclear reactor.

* * * * *